United States Patent [19]

Masuda et al.

[11] 4,001,257
[45] Jan. 4, 1977

[54] PROCESS FOR PRODUCING NICOTINIC ACID

[75] Inventors: Keiji Masuda; Hidenori Kizawa, both of Nakago; Yasuhiko Otaki, Joetsu, all of Japan

[73] Assignee: Nippon Soda Company, Ltd., Tokyo, Japan

[22] Filed: Aug. 8, 1975

[21] Appl. No.: 603,133

Related U.S. Application Data

[63] Continuation-in-part of Ser. No. 303,028, Dec. 2, 1972, abandoned.

[52] U.S. Cl. .................................. 260/295.5 R
[51] Int. Cl.$^2$ .................................. C07D 213/55
[58] Field of Search ............... 260/295.5 R, 295 R

[56] References Cited

UNITED STATES PATENTS

| 3,657,259 | 4/1972 | Stocker et al. ............... 260/295 R |
| 3,741,976 | 6/1973 | Stocker et al. ............... 260/295.5 R |

Primary Examiner—Alan L. Rotman
Attorney, Agent, or Firm—George B. Oujevolk

[57] ABSTRACT

Nicotinic acid is produced by oxidizing dialkylpyridine such as 2-methyl-5-ethylpyridine, 2,5-lutidine and the like, with nitric acid by an amount of 100 to 118 percent, preferably 100 to 108 percent, to the theoretical oxidizing amount, at a temperature of 220° to 240° C, preferably 225 to 235° C under a pressure of 30 to 45 kg/cm$^2$ for 5 to 30 minutes.

6 Claims, 1 Drawing Figure

PROCESS FOR PRODUCING NICOTINIC ACID

CROSS-REFERENCE TO RELATED APPLICATION

This application is a continuation-in-part of U.S. application Ser. No. 303,028, filed on Dec. 2, 1972, now abandoned.

BACKGROUND OF THE INVENTION

The present invention relates to a process for the production of nicotinic acid by oxidizing di-alkylpyridine, i.e., 2-methyl-5-ethyl pyridine, 2,5-lutidine, 2-methyl-5-butyl pyridine and 2-propyl-5-ethyl pyridine, and more particularly to a process of producing nicotinic acid continuously with a nitric acid oxidation procedure without intricate post-treatment.

Nicotinic acid is a very important industrial product as a medication and an additive of foodstuff or feedstuff. Generally, it is made by oxidizing dialkylpyridine, paticularly 2-methyl-5-ethylpyridine (hereinafter 2-methyl-5-ethyl pyridine is abbreviated as MEP), and then decarboxylating the resulting oxidized compound and finally obtaining nicotinic acid. Further, as its oxidizing agent, air, sulphuric acid-nitric acid or nitric acid or the like is employed.

Except for the process using nitric acid as an oxidizing agent, the above mentioned processes have defects using as the formation of numerous secondary reaction products, impurities or colored finished products, and an inferior yield, and those processes are not practically employed as an industrial producing process.

Also, even the process that is an oxidizing procedure with nitric acid, and is the unique industrial process at present, gives an inferior yield or requires intricate operational steps or produces a poorly colored product, and is, therefore, still unsatisfactory as an industrial process.

The various processes heretofore known which comprise oxidizing MEP with nitric acid are summarized and classified roughly into the following three processes:

a. A process for producing nicotinic acid with two steps which comprise producing isocinchromeronic acid containing nicotinic acid, (the said isocinchomeronic acid is hereinafter abbreviated as (ICMA), in the first step and then applying a decarboxylating step to said isocinchomeronic acid after separating ICMA or with separating ICMA and thus obtaining nicotinic acid in the second step.

The reaction is carried out by oxidizing MEP with nitric acid by an amount of 90 to 117 percent to the theoretical oxidizing amount at a temperature of 175° C to 200° C under a gauge pressure of 18 to 35 kg/cm² and thereby a resulting reaction solution containing mainly ICMA is obtained; and further, according to the process described in U.S. Pat. No. 2,702,802 and Zh. Prikl Khim 39(6)1388-94 (1966), U.S. S. R., the said ICMA is separated from the resulting reaction solution and a decarboxylating reaction is carried out in another reactor; and further, according to the process of French Patent Nos. 1,509,049 and 1,509,120, ICMA is not separated from the resulting reaction solution and the decarboxylating reaction is carried out at a temperature of 205° C to 235° C under pressure of 20 to 35 kg/cm², and thus a solution containing nicotinic acid is obtained.

The separation of nicotinic acid from the reaction solution is carried out by neutralizing the reaction solution with a basic material to a pH value of 3.3 to 3.5 and cooling the reaction solution and crystallizing nicotinic acid.

According to these processes, nicotinic acid is crystallized as a product containing impurities and consequently, the product must be further purified and the operation for collecting unreacted MEP and nicotinic acid from a separated mother liquid is complicated. Furthermore, the reaction operation for the above process is carried out by two steps and additionally, an inferior yield of 70 percent or less acts as a drawback. The finished product obtained above is remarkably colored with a yellowish color and cannot be immediately used as a satisfactory finished product.

b. Another process, a process for continuously producing nicotinic acid is described in U.S. Pat. No. 2,708,196, which comprises taking out continuously a reaction solution containing ICMA and nicotinic acid from a reaction mixture, and further separating ICMA from the reaction solution and then using it recurrently for an initial reaction. Nicotinic acid is crystallized as a nitrate salt of nicotinic acid from a mother liquor, from which ICMA was separated. (Hereinafter, nitrate salt of nicotinic acid is abbreviated as NA-HNO₃).

In the process, MEP is oxidized with nitric acid by an amount of 115 to 125 percent in proportion to the theoretical oxidizing amount of MEP at a temperature of 180° C to 185° C under a gauge pressure of 18 to 20 kg/cm² and a reaction solution containing ICMA and NA-HNO₃ is obtained, and then the reaction solution is continuously taken out and cooled at 35° C for a sufficient length of time to separate ICMA. The ICMA is recurrently fed into a repeating step of the oxidizing reaction. On the other hand, a mother liquor containing NA-HNO₃ and free of ICMA is cooled at a temperature ranging from 0° C to −5° C to separate NA-NHO₃ from the mother liquor. But, the mother liquor, from which NA-HNO₃ is once separated, still contains a large amount of NA-HNO₃, so that the mother liquor is further concentrated and thereby, NA-HNO₃ is collected from it. The NA-HNO₃ obtained is treated by adding a basic material in it and a pH value of the resulting solution is adjusted in a range around an isoelectric point of nicotinic acid and then nicotinic acid is crystallized and separated by cooling it.

This process requires a long time for the step of separating ICMA, the step of separating NA-HNO₃ and further the step of separating, crystallizing nicotinic acid, and furthermore this is a process requiring intricate operations, so that this process is unsatisfactory as an industrial process.

c. Another improved process which is adapted from the previous process (b) is provided by West German Patent No. 1,956,117 and Japanese Patent Publication No. 15944/1971.

This process is superior, because a high yield of 80 to 85 percent is attained and ICMA does not remain in a reaction terminated solution.

The process comprises carrying out the reaction by using nitric acid by an amount of 130 to 165 percent to the theoretical oxidizing amount of MEP at a temperature of 235° C to 330° C under a pressure of 50 to 280 kg/cm².

This process does not necessitate the operation of separating ICMA but requires intricate operations for separating NA-HNO₃ from the reaction solution and further separating, crystallizing nicotinic acid from it, such as revealed in the previous process (b). Therefore, this process is also unsatisfactory as an industrial producing process.

Another recent process is described by August Stocker et al in U.S. Pat. Nos. 3,657,259 and 3,741,976 directed to the production of the pyridine carboxylic acid hydronitrate. In this process it is necessary to separate the hydronitrate, dissolve it in ater, adjust the pH thereof to the isoelectric point of the desired acid product and recrystallize it therefrom.

The invention as well as other objects and advantages thereof will be more apparent from the following detailed description when considered with the accompanying drawings, in which:

DETAILED DESCRIPTION

Figure 1:
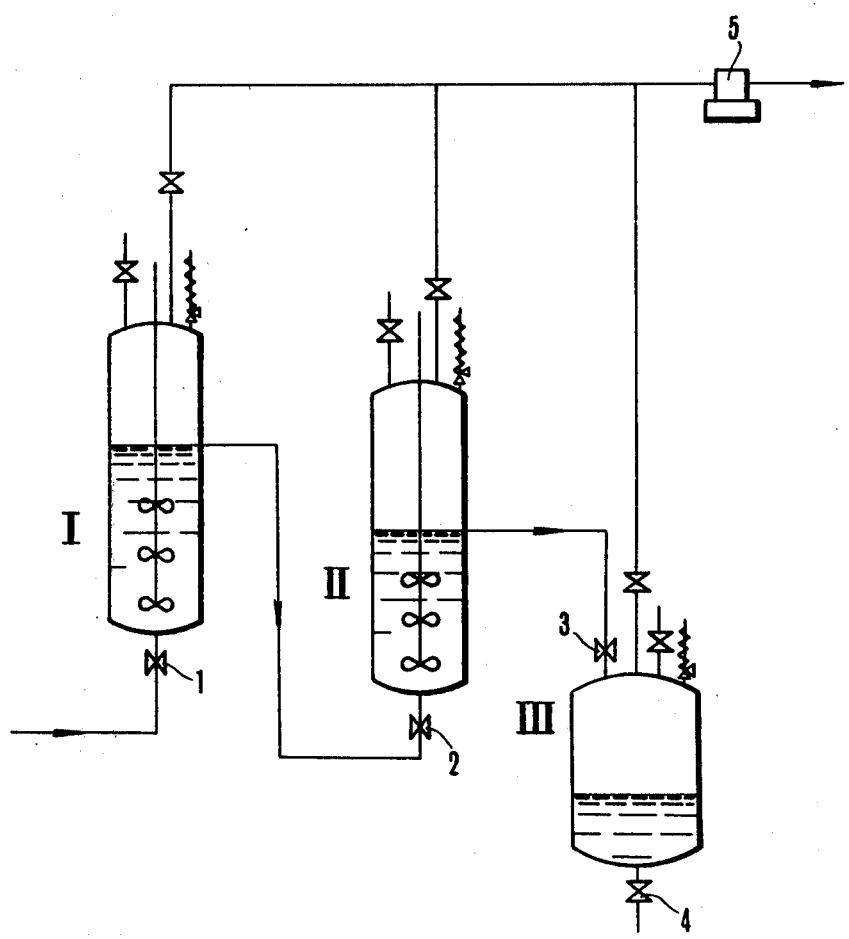
FIG. 1 shows a sketch of a reaction apparatus for the present invention.

In FIG. 1, No. I and No. II show a reactor and No. III shows a receiving tank of reaction solution. No. 1 is a charging inlet of raw material, No. 2 is an introducing inlet feeding a reaction solution from the reactor I, No. 3 is a receiving inlet of reaction solution, No. 4 is an outlet of the reaction solution, and No. 5 is a valve for adjusting pressure.

The inventors carried out extensive research on an advantageous process from the viewpoint of industrial production, in other words, the inventors carried out the research for removing the numerous drawbacks from the processes hereinbefore described which comprises producing nicotinic acid by applying the nitric acid oxidation step to MEP.

As a result, the inventors have accomplished the present invention which is very advantageous for industrial production of nicotinic acid.

According to the present invention, nicotinic acid is produced by oxidizing dialkylpyridine, such as MEP, with nitric acid by an amount of 100 to 118, preferably 100 to 108 percent, to the theoretical oxidizing amount at a temperature of 220° t 240° C, preferably 25° to 235° C under a pressure of 30 to 45 kg/cm² for 5 to 30 minutes.

The inventors discovered that, if the reaction is carried out under the selected reaction conditions described, a resulting reaction solution being entirely free from ICMA is obtained and the pH value of said reaction solution indicates directly the isoelectric point of nicotinic acid or its adjacent point. (According to the present invention, the said adjacent point is confirmed in a range of 1.5 to 3.5).

Hitherto, in a process for producing nicotinic acid using a theoretical amount or a small excess of nitric acid, the idea that the ICMA always remains in the reaction terminated solution has been the opinion of persons skilled in the art. The above fact that the inventors have found was contrary to the common sense of persons skilled in the art. The present invention is accomplished by selecting narrow reaction conditions.

Consequently, in the case of crystallizing and separating nicotinic acid from the reaction in compliance with the present invention, conventional intricate separating operations are not required.

A highly pure nicotinic acid can be easily crystallized and separated from the reaction solution by concentrating and cooling said reaction solution. In case that pH value of the reaction solution is low, adjusting the pH before cooling is preferable.

In the course of research for the present invention, the inventors discovered that a pH value of the resulting reaction solution changes variously according to the reaction conditions. The inventors carried out further researches and as a result, the inventors discovered that the pH vaue of the resulting reaction solution sometimes indicates a range of 4 to 5 on the alkaline side in contrast to the isoelectric point and further, on another occasion, indicates a range of 1 to 2 on the acid side, and further, the pH value under some particular reaction conditions indicates a range of 3.0 to 3.3 of the isoelectric point of nicotinic acid, (this figure is also mentioned hereinafter), and then, in this occasion, by only cooling the reaction solution, a high purity of nicotinic acid can be directly crystallized and separated.

On the basis of the foregoing discovery, the inventors carried out research on a choice of reaction conditions, in other words, what reaction conditions shall be selected for keeping the pH value of the reaction terminated solution in a range of the isoelectric point of nicotinic acid, and thus, the inventors accomplished the present invention.

According to the research results of the inventors, if the resulting reaction solution indicates a pH value of higher than 3.5 this reaction condition is regarded as a severe case. The higher pH vaue is due to the consumption of the excess nitric acid in a side reaction of a reacted organic material and further, the occurrence of pyridine by decomposition of produced nicotinic acid. On the contrary, if the resulting reaction solution indicates a pH value of lower than 1.5, this reaction condition is regarded as a mild case and even if a large amount of MEP, i.e., unreacted base remains, a furthermore large amount of unreacted nitric acid in the excess to the said amount of MEP remains, and this is regarded as the reason. Moreover, the oxidation and decarboxylation reactions proceed effectively under the reaction condition of present invention. The reaction is terminated with a minor occurrence of unreacted materials and decomposed materials. From the results, it is considered that a pH value for the resulting reaction solution may be maintained in a most optimum range of the isoelectric point of nicotinic acid or around its range, where nicotinic acid can be directly or easily separated from the resulting reaction solution.

The isoelectric point of nicotinic acid is disclosed in numerous literature as a pH value in a range of 3.0 to 3.3. But, in the process of producing nicotinic acid relating to the present invention, it was found out that nicotinic acid can be obtained with a high yield not only in the pH range of 3.0 to 3.3, but also in the pH range of 1.5 to 3.5 of the resulting reaction solution, so that, this pH range of 1.5 to 3.5 is selected in the present invention. A range around an isoelectric point of nicotinic acid which is stated in the present invention is defined as the pH range of 1.5 to 3.5. Hereinafter, the present invention is more minutely explained.

1. An employable amount of nitric acid:

As to an employable amount of nitric acid, the theoretical amount is desirable, but it may give a pH value of higher than 3.5 to the resulting reaction solution under some reaction conditions and thereby the yield may deteriorate. In this occasion, a surplus amount of nitric acid shall be used, so that nitric acid by an amount of 100 to 118 percent of the theoretical amount, preferably 100 to 108 percent, is used for the present invention.

If the nitric acid by an amount of more than 118 percent is employed, the yield decreases and nicotinic acid must be separated as NA-$HNO_3$ in an industrial process. In case the amount of nitric acid is less than 100 percent of the theoretical amount, the yield is also low.

The nitric acid is usually 20 to 30 weight percent aqueous.

2. Reaction temperature.

A reaction temperature in a range of 220° to 240° C, preferably 25° to 235° C, is effectively selected for the present invention. The choice of reaction temperature for the present invention, together with the choice of the amount of nitric acid to be employed in the previous paragraph (1) is considered as one of the most important reaction conditions. In other words, a higher temperature than 240° C gives a severe reaction condition and thereby a produced reaction compound is decomposed and nicotinic acid obtained contains a large amount of impurities, and simultaneously results in an inferior yield. Also, the yield decreases at a lower temperature than 220° C.

3. Reaction time.

A reaction time in a range of 5 to 30 minutes is most effectively used for the present invention. The reaction time is the third important reaction condition in relation to the amount of nitric acid (1) and the choice of reaction temperature (2). Therefore, the reaction time is selected on the basis of the choices for the amount of nitric acid (1) and the reaction temperature (2) or in the correlation to the other reaction conditions.

In case of less than 5 minutes the reaction is imperfectly carried out and, in case of more than 30 minutes the reaction compound is decomposed, a favourable result can not be obtained.

4. Reaction pressure.

A reaction pressure in a range of 30 to 45 kg/cm² is effectively used for the present invention, but compared with an employable amount of nitric acid (1), a reaction temperature (2) and a reaction time (3), the reaction pressure is not an important condition. In other words, the reaction pressure almost depends on the amount of nitric acid (1), the reaction temperature (2), and the reaction time (3) and particularly depends on the reaction temperature (2).

5. pH value range of a resulting reaction solution:

If the reaction for the present invention is carried out under the above specified reaction conditions, the pH value of the resulting reaction solution approximately indicates the isoelectric point of nicotinic acid or somewhere around said isoelectric point, in other words, a pH range of 1.5 to 3.5. Above this pH range means that, if the reaction is completely finished while maintaning this pH range, a high purity nicotinic acid can be easily crystallized and separated from a reaction solution with a high yield by only concentrating and then cooling the resulting reacton solution, or by only adjusting the pH value after concentration of said solution by adding a little basic materials and then cooling it. Therefore, the maintenance of the above pH range which is attained by the selection of the reaction conditions of the present invention is very important and it can be said to be a fundamental condition of the present invention. The raw material, pyridine base, is usually used as the basic material.

(Further, if the reaction is carried out under unspecified reaction conditions, other than the reaction conditions of the present invention, the pH value of the reaction terminated solution in some cases may indicate the above mentioned range of 1.5 to 3.5, but on this occasion, the yield deteriorates).

6. Reaction apparatus.

The process for continuously producing nicotinic acid in accordance with the present invention is carried out by using the reaction apparatus shown in FIG. 1.

A liquid mixture consisting of a raw material, i.e., MEP and nitric acid is continuously fed into reactor I and II from an inlet of raw material 1, where said liquid mixture is maintained under the mentioned reaction conditions and further, the said reactors I and II are preliminarily heated at the specified reaction temperature.

A reaction solution in the course of the specified reaction time (or the specified stagnation time) is collected in receiving tank III of the reaction solution.

The reactors I and II are fitted wih a heating mantle, an agitator, a degasifying valve and a thermometer.

A liquid reaction product treated under the specified reaction conditions is taken out from the receiving tank of the reaction solution and the reaction product (terminated reaction solution) is concentrated by evaporation and then it is cooled at 0° C to 5° C. In case the pH value of the resulting reaction solution is low, for example, pH range of 1.5 to 2.5, a pH adjustment is carried out by adding a little basic materials to the solution which is previously concentrated and then the cooling step is carried out.

The nicotinic acid which has crystallized is separated and dried so that a high quality of nicotinic acid having a purity of higher than 99 percent is obtained.

The mother liquor containing a nicotinic acid residue, from which a large amount of nicotinic acid has already separated, is treated by a process that the mother liquor is further concentrated and it is added to a subsequent separating step and then it is collected, otherwise MEP and nitric acid are added in the mother liquor to prepare the starting material mixture having a specified concentration and then it is re-used.

According to the process of the present invention, the nicotinic acid can be obtained as a high quality product having a purity of higher than 99 percent and can be easily purified to a 99.9 percent of high purity product, pure-white product, by conventional purifying method, i.e., the purification with active carbon.

According to the process of the present invention, a conversion ratio of MEP may reach a rate of about 90 percent or more and the separation ratio of nicotinic acid may reach a rate of about 80 to 85 percent which is based on its conversion ratio and further, referring to the total yield rate, it reaches a rate of about 90 percent.

In comparison with conventional producing processes, the process of the present invention is a very advantageous continuous producing process from the viewpoint of industrialization, in which the occurrence of ICMA eliminated, in other words, the steps of separating IcMA, collecting and re-using it are not required and further, a high purity of nicotinic acid can be separated directly or easily from a reaction solution with a high yield.

Moreover, it will be understood by persons skilled in the art that a di-alkyl-pyridine other than MEP, i.e., 2,5-lutidine, 2-methyl-5-butyl pyridine and 2-propyl-5-ethyl pyridine can also be effectively used for producing nicotinic acid relating to the process of the present invention as a raw material.

EXAMPLES

For the purpose of giving those skilled in the art a better understanding of the invention, the following illustrative examples are given:

All percents in the Examples are weight percents:

Example 1 to 5

A mixture of MEP and aqueous nitric acid was continuously fed into a pipe reactor having a diameter of 3 cm, and the reactions were carried out under the respective reaction conditions as in Table 1.

The resulting reaction solutions indicated a pH value of 1.6 to 2.4.

After concentration of each reaction solution, the pH of the solution was adjusted to 3.2 by adding MEP, and then each reaction solution was cooled at 0° C to 5° C. The crystallized nicotinic acid of each example was separated by filtration.

The results are shown in Table 1.

Comparative Example 1 to 2

MEP and nitric acid by an amount of 95.8% and 33% to the theoretical amount (6 mole per 1 mole of MEP) was reacted and worked up as in Example 1.

The results are shown in Table 1.

Exaple 6

A mixture of MEP and 25% nitric acid was reacted at a various temperature and worked up as in Example 1. The results are shown in Table 2.

Table 2

| Test No. | Ratio of nitric acid per theoretical amount (%) | Reaction condition | | | Conversion ratio of MEP (%) | Nicotinic acid | |
|---|---|---|---|---|---|---|---|
| | | Temperature (° C) | Pressure (kg/cm$^2$) | Time (Min.) | | Purity | Total yield based on the conversion ratio (%) |
| 1 | 100 | 205 | 35 | 40 | 94.1 | 99.8 | 81.0 |
| 2 | " | 215 | 35 | 30 | 93.2 | 99.6 | 82.5 |
| 3 | " | 225 | 35 | 15 | 90.0 | 99.6 | 86.9 |
| 4 | " | 230 | 38 | 14 | 89.8 | 99.8 | 89.1 |
| 5 | " | 235 | 38 | 12 | 90.4 | 99.8 | 91.8 |
| 6 | " | 240 | 39 | 10 | 92.2 | 99.8 | 80.4 |
| 7 | 108 | 205 | 35 | 30 | 93.2 | 99.7 | 78.2 |
| 8 | " | 215 | 35 | 30 | 94.0 | 99.8 | 80.1 |
| 9 | " | 225 | 35 | 15 | 90.5 | 99.6 | 83.0 |
| 10 | " | 230 | 38 | 14 | 91.0 | 99.8 | 91.0 |
| 11 | " | 235 | 38 | 12 | 90.1 | 99.8 | 90.8 |
| 12 | " | 240 | 40 | 9 | 93.4 | 99.7 | 80.0 |

We claim:

1. A process for the production of nicotinic acid which consists essentially of the steps of reacting 2-methyl-5-ethylpyridine with an amount of nitric acid which is 100 to 108 weight percent of that theoretically required to oxidize the 2-methyl-5-ethylpyridine to nicotinic acid, at a temperature of 225° C. to 235° C. and a pressure of 30 to 45 kg/cm$^2$ for 5 to 30 minutes, to oxidize said 2-methyl-5-ethylpyridine to nicotinic acid, while maintaining the pH of the reaction mixture at 1.5 to 3.5, concentrating the resulting reaction mixture while maintaining the pH thereof at 1.5 to 3.5, cooling the concentrated reaction mixture to precipitate nicotinic acid, and separating the nicotinic acid having a purity of at least about 98 percent and in a yield of at least about 85 to 90 weight percent.

2. A process for the production of nicotinic acid which consists essentially of the steps of reacting di-lower alkyl pyridine with an amount of nitric acid which is 100 to 118 weight percent of that theoretically required to oxidize the di-alkyl pyridine to nicotinic acid at a temperature of 220° to 240° C and a pressure of 30–45 kg/cm$^2$ for 5 to 30 minutes, to oxidize said di-alkyl pyridine to nicotinic acid, while maintaining the pH of the reaction mixture at 1.5 to 3.5; concentrating the resulting reaction mixture while maintaining the pH thereof at 1.5 to 3.5; cooling the concentrated reaction mixture to precipitate nicotinic acid and sepa- Table 1

| Examples | Nitric Acid | | Reaction conditions | | | pH value of reaction solution | Conversion ratio of MEP (%) | Nicotinic acid | | |
|---|---|---|---|---|---|---|---|---|---|---|
| | Concentration (%) | Ratio per theoretical amount (%) | Temperature (° C) | Pressure (kg/cm$^2$) | Time (min.) | | | separated yield based on the conversion ratio (%) | Purity (%) | Total yield based on the conversion ratio (%) |
| 1 | 25 | 100 | 225 | 32 | 17 | 1.9 | 90.0 | 80.0 | 99.6 | 86.9 |
| 2 | 25 | 100 | 233 | 38 | 12 | 2.1 | 90.4 | 82.5 | 99.8 | 91.4 |
| 3 | 25 | 108 | 233 | 38 | 12 | 2.1 | 90.1 | 82.9 | 99.8 | 90.8 |
| 4 | 25 | 108 | 230 | 38 | 16 | 2.4 | 91.0 | 81.3 | 99.8 | 91.0 |
| 5 | 20 | 118 | 233 | 39 | 11 | 1.6 | 93.6 | 79.2 | 99.5 | 85.4 |
| Comparative Example 1 | 25 | 95.8 | 230 | 38.5 | 14 | 2.4 | 88.2 | 72.2 | * | 79.1 |
| " 2 | 20 | 133 | 240 | 42 | 9 | 0.3 | 98.2 | 71.6 | 99.6 | 80.3 |

(* yellowish brown)

rating the nicotinic acid, having a purity of at least about 98 percent and in a yield of at least about 85 to 90 weight percent.

3. A process according to claim 2, wherein the dialkylpyridine is 2-methyl-5-ethylpyridine.

4. A process according to claim 2, wherein the amount of nitric acid is 100 to 108 percent to the theoretical amount.

5. A process according to claim 2, wherein the reaction is carried out at a temperature of 25° to 235° C.

6. A process according to claim 2, wherein after adjusting the pH of the concentrated reaction mixture to the isoelectric point of nicotinic acid with said dialkylpyridine, the concentrated reaction mixture is cooled to precipitate nicotinic acid.

* * * * *